United States Patent [19]

Bourne

[11] Patent Number: 4,621,074

[45] Date of Patent: Nov. 4, 1986

[54] METHOD OF TREATING SMOKING WITHDRAWAL SYNDROME

[76] Inventor: Stephen J. Bourne, 109 Grange Crescent, Chigwell, Essex, England

[21] Appl. No.: 792,264

[22] Filed: Oct. 28, 1985

[51] Int. Cl.⁴ ............................................. A61K 37/00
[52] U.S. Cl. ..................................... 514/12; 514/813
[58] Field of Search ................................. 514/813, 12

[56] References Cited

U.S. PATENT DOCUMENTS

| | | | |
|---|---|---|---|
| 3,036,956 | 5/1962 | Thompson | 514/12 |
| 4,164,560 | 8/1979 | Folkman et al. | 424/22 |
| 4,344,431 | 8/1982 | Yolles | 128/260 |
| 4,357,312 | 11/1982 | Hsieh et al. | 424/15 |
| 4,452,775 | 6/1984 | Kent | 424/19 |
| 4,555,397 | 11/1985 | Bachynsky | 424/10 |

OTHER PUBLICATIONS

Haggard, et al., *Science*, vol. 79, pp. 165–166 (1934).
Kershbaum, et al., *J.A.M.A.*, vol. 203, pp. 275–278 (1968).
Higenbottom, et al., *Thorax*, vol. 39, pp. 641–646 (1984).
Chem. Abst. 84: 116167y (1976)—Dressler et al.
Chem. Abst. 85: 182442(f) (1976)—Raffalt et al.

*Primary Examiner*—Douglas W. Robinson
*Attorney, Agent, or Firm*—Wood, Dalton, Phillips, Mason & Rowe

[57] ABSTRACT

A method of treatment to reduce or eliminate the symptoms of smoking withdrawal syndrome in tobacco smokers comprising the administration of at least one dose of a corticotrophin or a corticotrophin analog.

7 Claims, No Drawings

METHOD OF TREATING SMOKING WITHDRAWAL SYNDROME

BACKGROUND OF THE INVENTION

This invention relates to a method of treatment to reduce or eliminate the symptoms of smoking withdrawal syndrome in tobacco smokers and thereby make it easier for them to stop smoking.

Known methods of treating tobacco addiction have met with limited success. Anti-smoking clinics using a variety of methods report a long term success rate of from 10% to 20% (Higenbottom T. and Chamberlain A. (1984) *Thorax*, 39, 641-646).

To date no attempt to treat tobacco addiction by a clinical approach based on an understanding of the physiological effects of nicotine has been reported.

The immediate physiological effect of nicotine inhalation is a temporary rise in blood sugar which produces the 'lift' experienced by smokers (Haggard H. and Greenberg L. (1934) *Sience*, 79, 165-166). This rise in blood sugar is the result of an increased output of glucocorticoids by the adrenal cortex in response to stimulation by endogenous corticotrophin secreted by the anterior pituitary gland in response to unphysiological stimulation with nicotine (Kershbaum A. et al. (1968) *J.A.M.A.*, 203, 275-278). It therefore appears that the lift associated with smoking is initiated by the secretion of corticotrophin.

It is possible that in smokers the capacity of the anterior pituitary gland to produce normal quantities of corticotrophin is impaired by repeated unphysiological stimulation with nicotine. This would result in secondary hypoadrenocorticism and a consequent reduced output of glucocorticoids with a tendency to hypoglycaemia. The later would result in a reflex increase in adrenaline production which would tend to simultaneously correct the hypoglycaemia and cause feelings of nervous tension. The hunger caused by the low blood sugar and the nervous tension caused by the extra circulating adrenaline may be the basis of smoking withdrawal syndrome. Relief of these symptoms by nicotine inhalation is believed to be the result of nicotine-stimulated secretion of endogenous corticotrophin.

SUMMARY OF THE INVENTION

It is an object of the present invention to provide a method of treatment to reduce or eliminate the symptoms of smoking withdrawal syndrome and thereby make it easier for smokers to stop smoking.

I have now found that relief from the symptoms of smoking withdrawal syndrome can be obtained by the administration of a corticotrophin or a corticotrophin analog. Treatment can be by high; or low; dosage therapy.

The term "corticotrophin" is used hereinafter to refer to a corticotrophin or a corticotrophin analog.

DETAILED DESCRIPTION OF THE INVENTION

The present invention is concerned with a method of treatment to reduce or eliminate the symptoms of smoking withdrawal syndrome in tobacco smokers which comprises the administration of at least one dose of corticotrophin by any suitable means. These include, for example, administration by intramuscular, subcutaneous, transdermal, transthecal, or intravenous injection, administration orally, transnasally, or percutaneously, or administration by inhalation. The preferred method of administration depends on the form in which the corticotrophin is available. Any suitable form of corticotrophin can be used in the method of the invention; preferred forms include, for example, ACTH/CMC, Cortrosyn, Synacthen, Acthar Gel, Cortrosyn Depot, and Synacthen Depot (Cortrosyn, Synacthen, Acthar Gel, Cortrosyn Depot, and Synacthen Depot are Trade Marks).

For both high and low dosage therapies by the method according to the invention, the corticotrophin is preferably in the form of a depot composition, such as a gel, and the preferred method of administration is by intramuscular injection.

In a preferred method of treatment by means of high dosage therapy, a single dose of depot corticotrophin is administered, preferably in an amount of 180 i.u. A single dose of corticotrophin usually reduces the symptoms of smoking withdrawl syndrome sufficiently to enable the patient to stop smoking. In a small proportion of patients, mild withdrawal symptoms are experienced several days after the original treatment and administration of a further dose of depot corticotrophin is required to eliminate the remaining symptoms and enable the patient to stop smoking. This second dose of corticotrophin is usually administered three to six days after the administration of the first dose. The preferred amount of corticotrophin in the second dose is 80 i.u.

In a preferred method of treatment by means of low dosage therapy, a series of doses of depot corticotrophin are administered at intervals over a period of up to ten days. A preferred course of treatment consists of three intramuscular injections of 80 i.u. of depot corticotrophine which are administered at intervals of approximately every three days. Three doses of corticotrophin are usually sufficient to enable the patient to stop smoking. A small proportion of patients experience mild withdrawal symptoms several days after the completion of the original course of treatment and these patients are given further doses of depot corticotrophin over the following weeks. A preferred course of further treatment in such cases is the administration of 40 i.u. doses of depot corticotrophin at intervals of approximately every three days until the remaining symptoms have been eliminated (usually 2-4 weeks after completion of the initial treatment).

RESULTS

Ten smokers, who had previously been unable to stop smoking because of severe withdrawal syndrome, were each given a single intramuscular injection of 180 i.u. of corticotrophin in the form of Acthar Gel. After this injection, nine of the patients stopped smoking and the remaining patient reduced his consumption from 80 to 30 cigarettes a day. This patient and three others who complained of the return of mild withdrawal symptoms were each given booster injections of 80 i.u. of Acthar Gel three to six days after the original injection. After the second injection the remaining smoker also stopped smoking; all ten patients were still not smoking seven months after the treatment. At this time, half the patients had experienced some weight gain.

Further details of the patients and their treatment are given in the following table.

TABLE I

Patients treated with corticotrophin for cigarette smoking.

| Age/Sex | No. smoked/day | Years smoked | Day of booster | Wt. gain in lbs-7 months after treatment |
|---|---|---|---|---|
| 36/F | 20 | 19 | — | 14 |
| 38/M | 40 | 20 | — | 7 |
| 45/M | 25 | 25 | 3 | — |
| 37/M | 25 | 17 | — | 21 |
| 24/M | 10 | 10 | — | 7 |
| 38/F | 25 | 5 | 6 | — |
| 50/M | 10 | 25 | — | — |
| 70/M | 80 | 50 | 6 | — |
| 49/F | 60 | 30 | — | 14 |
| 52/F | 20 | 33 | 6 | — |

The method of the invention provides a cheap and effective treatment for smoking withdrawal syndrome and makes it easier for patients to stop smoking.

Whilst details of preferred active materials and preferred dosage regimes have been given above, it will be understood that the present invention is not limited thereto. Given the foregoing teaching, the choice of other suitable active materials of the kind referred to and other suitable dosage regimes will be within the knowledge of physicians and others skilled in the art.

What is claimed is:

1. A method of reducing or eliminating the symptoms of smoking withdrawal syndrome in tobacco smokers, which method comprises the administration in an effective amount of at least one dose of a corticotrophin or a corticotrophin analog.

2. The method of claim 1 wherein administration of said dose is effected by injection of a depot composition.

3. The method of claim 2 wherein a single dose of 180 i.u. of corticotrophin is administered.

4. The method of claim 2 wherein a first dose of 180 i.u. of corticotrophin and after an interval of 3 to 6 days a second dose of 80 i.u. of corticotrophin are administered.

5. The method of claim 2 wherein a series of doses of 80 i.u. of corticotrophin are administered over a period of up to 10 days.

6. The method of claim 2 wherein a series of three doses of 80 i.u. of corticotrophin are administered at intervals of approximately 3 days.

7. The method of claim 2 wherein a series of three doses of 80 i.u. corticotrophin are administered at intervals of approximately 3 days and then a series of doses of 40 i.u. of corticotrophin again at intervals of approximately 3 days.

* * * * *